United States Patent
Muehlhoff et al.

(10) Patent No.: US 10,925,770 B2
(45) Date of Patent: *Feb. 23, 2021

(54) SAFETY MECHANISM FOR LASER TREATMENT APPARATUS

(71) Applicant: Carl Zeiss Meditec AG, Jena (DE)

(72) Inventors: Dirk Muehlhoff, Jena OT Kunitz (DE); Carsten Lang, Eisenberg (DE); Karsten Festag, Jena (DE)

(73) Assignee: Carl Zeiss Meditec AG, Jena (DE)

( * ) Notice: Subject to any disclaimer, the term of this patent is extended or adjusted under 35 U.S.C. 154(b) by 557 days.

This patent is subject to a terminal disclaimer.

(21) Appl. No.: 15/166,326

(22) Filed: May 27, 2016

(65) Prior Publication Data
US 2016/0338876 A1 Nov. 24, 2016

Related U.S. Application Data

(62) Division of application No. 10/586,828, filed as application No. PCT/EP2006/000145 on Jan. 10, 2006, now Pat. No. 9,351,878.

(30) Foreign Application Priority Data

Jan. 11, 2005 (DE) ...................... 10 2005 001 249.3

(51) Int. Cl.
*A61F 9/009* (2006.01)
*A61F 9/008* (2006.01)
*A61B 90/00* (2016.01)

(52) U.S. Cl.
CPC .............. *A61F 9/009* (2013.01); *A61B 90/03* (2016.02); *A61F 9/00825* (2013.01);
(Continued)

(58) Field of Classification Search
CPC ...... A61F 9/008; A61F 9/009; A61F 9/00825; A61F 9/0084; A61F 2009/00872; A61B 90/03; A61B 2090/036
See application file for complete search history.

(56) References Cited

U.S. PATENT DOCUMENTS 4,061,423 A 12/1977 Pomerantzeff
4,984,916 A 1/1991 Sekine et al.
(Continued)

FOREIGN PATENT DOCUMENTS

DE 195 14 796 C1 9/1996
DE 198 31 674 A1 1/2000
(Continued)

OTHER PUBLICATIONS

Application and File History for U.S. Appl. No. 10/586,828, filed Jul. 20, 2006. Inventors: Muehlhoff et al.

Primary Examiner — Lynsey C Eiseman
Assistant Examiner — Amanda Steinberg
(74) Attorney, Agent, or Firm — Patterson Thuente Pedersen, P.A.

(57) ABSTRACT

A laser treatment unit for performing eye surgery, including a contact glass which can be placed onto the eye and through which a treatment laser beam (2) passes. A safety mechanism displaceably holds the contact glass such that the contact glass retreats when the contact glass is subjected to the action of a force contrary to the direction of incidence of the laser beam. The safety mechanism enables this retreating when a force is greater than a force limit value ($F_{min}$) and holds the contact glass in a fixed manner when the force is less than the force limit value.

26 Claims, 5 Drawing Sheets

(52) U.S. Cl.
CPC ....... *A61B 2090/036* (2016.02); *A61F 9/0084* (2013.01); *A61F 2009/00872* (2013.01)

(56) References Cited

U.S. PATENT DOCUMENTS

| | | | |
|---|---|---|---|
| 5,217,452 | A | 6/1993 | O'Donnell |
| 5,336,215 | A | 8/1994 | Hsueh et al. |
| 5,624,456 | A | 4/1997 | Hellenkamp |
| 5,952,843 | A * | 9/1999 | Vinh .................. G01R 1/07357 324/72.5 |
| 5,984,914 | A | 11/1999 | Cumming |
| 5,984,916 | A | 11/1999 | Lai |
| 6,027,454 | A | 2/2000 | Löw |
| 6,110,166 | A | 8/2000 | Juhasz |
| 6,149,643 | A * | 11/2000 | Herekar .................. A61F 9/008 606/10 |
| 6,245,058 | B1 * | 6/2001 | Suzuki .................... A61F 9/008 219/121.62 |
| 6,373,571 | B1 | 4/2002 | Juhasz et al. |
| 2002/0103481 | A1 * | 8/2002 | Webb ...................... A61F 9/009 606/5 |
| 2002/0103482 | A1 * | 8/2002 | Scholler ................. A61F 9/009 606/5 |
| 2005/0192562 | A1 * | 9/2005 | Loesel .................... A61F 9/009 606/5 |

FOREIGN PATENT DOCUMENTS

| | | |
|---|---|---|
| EP | 0 589 825 A2 | 3/1994 |
| EP | 0 608 052 A2 | 7/1994 |
| EP | 1 570 822 A1 | 9/2005 |
| WO | WO 03/002008 A1 | 1/2003 |

* cited by examiner

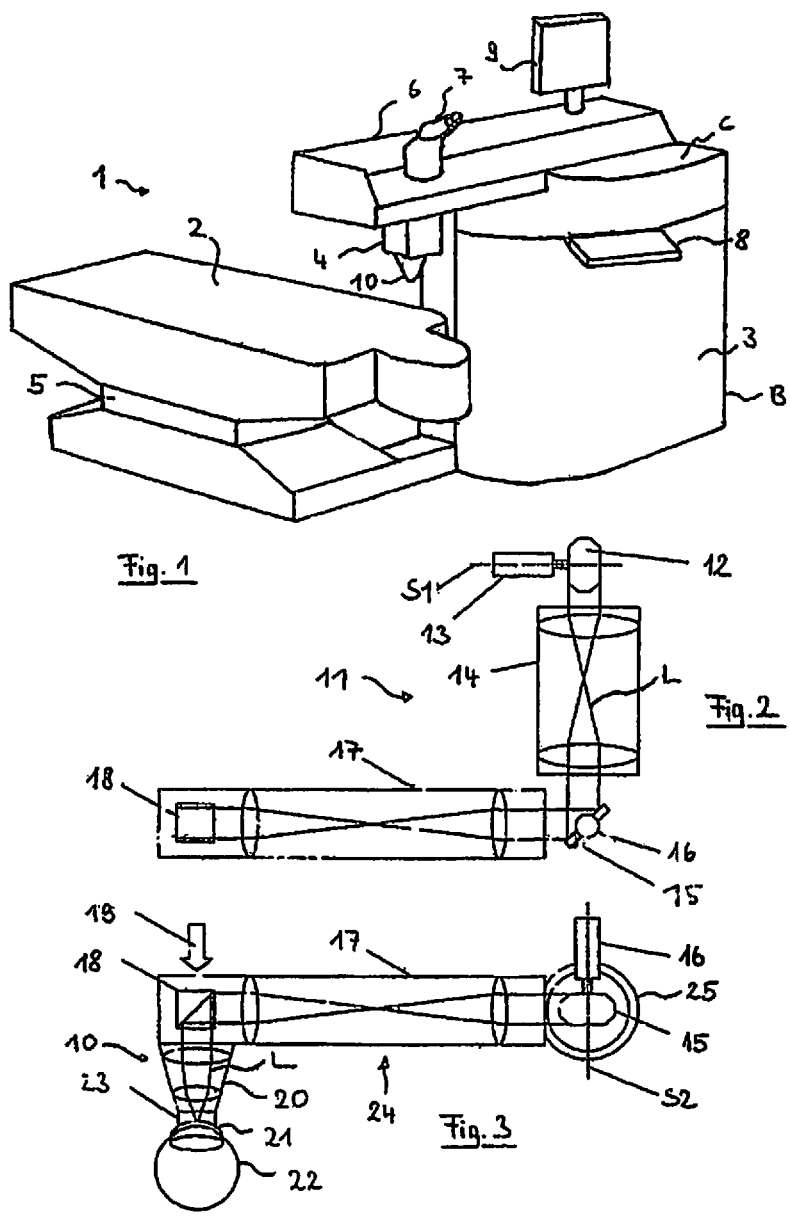

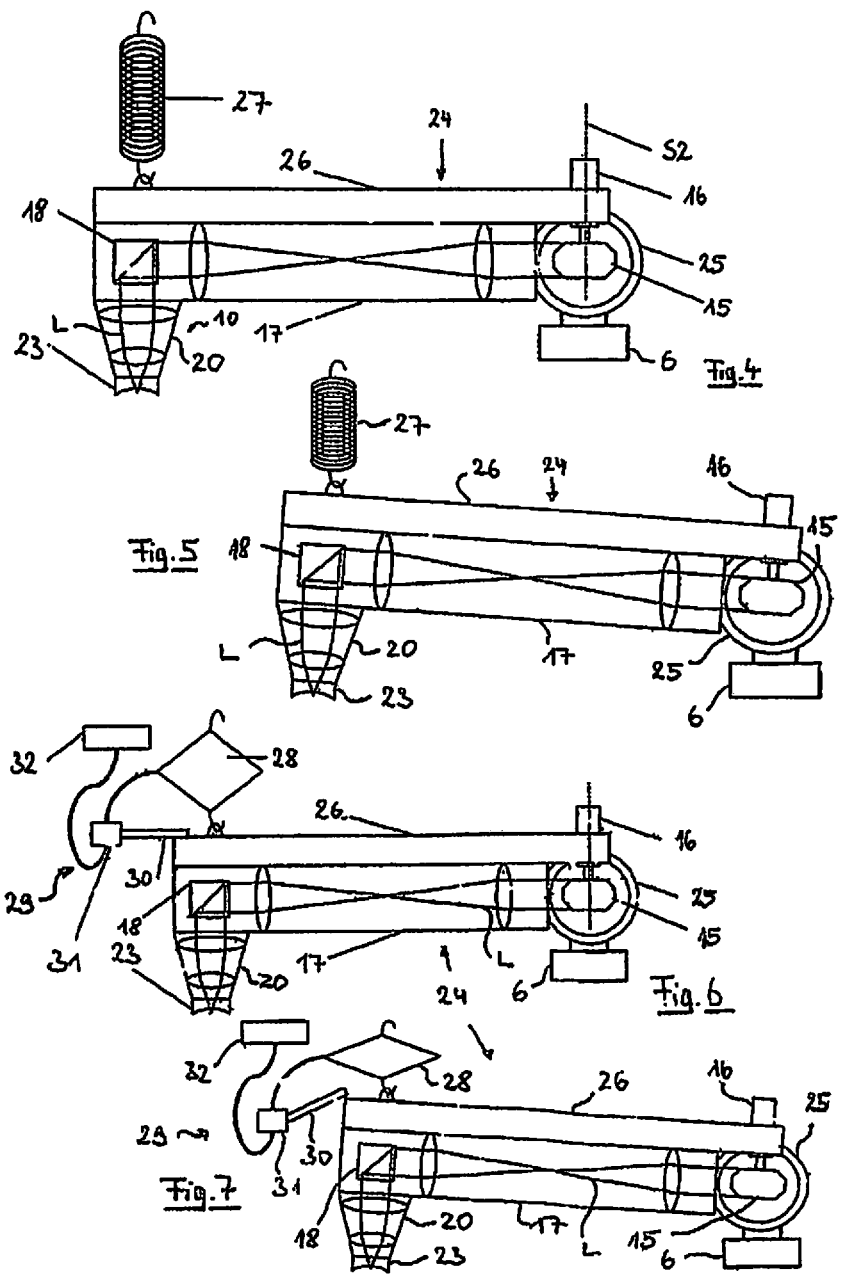

SAFETY MECHANISM FOR LASER TREATMENT APPARATUS

CROSS-REFERENCE TO RELATED APPLICATIONS

This application is a division of application Ser. No. 10/586,828, filed Jul. 20, 2006, now U.S. Pat. No. 9,351,878, issued May 31, 2016, entitled "Safety Mechanism for Laser Treatment Apparatus", which is a National Phase entry of PCT Application No. PCT/EP06/000145, filed Jan. 10, 2006, which claims priority from German Application No. 10 2005 001 249.3, filed Jan. 11, 2005, each of which is hereby fully incorporated herein by reference.

TECHNICAL FIELD

The invention relates to a laser treatment apparatus for ophthalmic surgery, said apparatus comprising a contact glass, which can be placed on the eye and through which a treatment laser beam is incident, and a safety mechanism holding the contact glass movable such that it retracts when a force is directed onto the contact glass counter to the direction of incidence of the laser beam. The invention further relates to a laser treatment apparatus for ophthalmic surgery comprising a beam-deflecting unit which variably deflects a treatment laser beam about at least one axis; focusing optics arranged following the beam-deflecting unit and focusing the laser beam into or onto the eye along an optical axis; a contact glass which can be placed on the eye and is arranged following the focusing optics, and a safety mechanism holding the contact glass movable such that it retracts when a force is directed onto the contact glass counter to the direction of incidence of the laser beam.

BACKGROUND

Such laser treatment apparatuses are used for laser-surgical methods on the eye. In doing so, the treatment laser radiation is focused such that an optical breakthrough causes changes to the tissue. The treatment laser radiation acts, for example, by photo-disruption or photo-ablation. A particularly advantageous application of these effects is found in correction of visual deficiency in ophthalmology. Visual deficiencies of the eye often result from the fact that the diffractive properties of the cornea and of the lens do not cause proper focusing on the retina. In the case of near-sightedness (also referred to as myopia), the focus of the relaxed eye is located in front of the retina, whereas in the case of far-sightedness (also referred to as hyperopia) the focus is located behind the retina. A visual deficiency can also be present in the form of an astigmatism if focusing is not effected in a focal point but with linear distortion.

For correction of visual deficiencies, it is known to suitably influence the diffractive properties of the cornea by means of treatment laser beams. Such methods are described, for example, in U.S. Pat. Nos. 5,984,916 and 6,110,166. In this case, a multiplicity of optical breakthroughs are sequentially arranged such that a partial volume is isolated within the cornea of the eye. This isolated partial volume, which is thus separated from the remaining corneal tissue, is then extracted from the cornea through a laterally opening cut. The shape of the partial volume is selected such that the diffractive properties of the cornea after removal of the partial volume are modified so that the desired correction of visual deficiencies is achieved.

In order to form the cut by sequential arrangement of optical breakthroughs, it is, of course, indispensable to generate the optical breakthroughs at exactly predetermined locations. This requires exact positioning of the laser beam in the cornea of the eye. Therefore, displacement of the eye relative to the laser treatment apparatus must be avoided or compensated for as far as possible. U.S. Pat. No. 6,373,571 and WO 0/002008 A1, therefore, propose contact lenses which are placed on the cornea of the eye as adapters and immobilize the eye relative to the laser treatment apparatus. The eye is usually secured to the adapter by suction using a vacuum. Such adapter, also referred to as contact glass, performs two functions: on the one hand, it deforms the eye in accordance with the adapter's predetermined surface shape. Thus, a defined surface shape is present in the beam path of the laser treatment apparatus. On the other hand, the contact glass fixes the eye and thereby prevents displacement of the eye during therapeutic intervention.

In order to hold the contact glass securely to the eye even when the patient moves, U.S. Pat. No. 5,336,215 proposes a device of the above mentioned type, wherein the lens focusing the laser radiation is seated in a frame together with a contact glass, which frame is in turn resiliently suspended. The lens and the contact glass are thus displaceable together along the optical axis of incidence of the treatment laser radiation. Any movement by the patient will thus automatically lead to a displacement of the contact glass and of the focusing optics in the beam path. Such movement of the optics has meanwhile turned out to be disadvantageous in terms of the quality with which the treatment laser beam can be focused.

As a remedy, it might be conceivable to mount the contact glass and the focusing optics permanently and irremovably to the laser treatment apparatus. However, this approach involves the risk of the eye being damaged by bruising when the patient moves. Such movement could either be caused by a physical movement of the patient or could occur when placing the eye in contact with the contact glass.

Therefore, it is an object of the invention to improve a laser treatment apparatus of the above-mentioned type such that the safety mechanism can reliably avoid squeezing of the eye without adversely affecting the optical quality of the laser treatment apparatus.

SUMMARY

This object is achieved in a laser treatment apparatus for ophthalmic surgery, said apparatus comprising a contact glass which can be placed on the eye and through which a treatment laser beam is incident, with a safety mechanism being provided which holds the contact glass movable on the housing such that the contact glass retracts when a force is directed onto the contact glass in a direction opposed to the direction of incidence of the laser beam, the safety mechanism enabling such retraction only in case of a force which exceeds a limit value of force and holding the contact glass fixed at a force which is below the limit value of force.

According to the invention, the object is further achieved by a laser treatment apparatus for ophthalmic surgery, said apparatus comprising a beam deflecting unit which variably deflects a treatment laser beam about at least one axis; focusing optics arranged following the beam-deflecting unit and focusing the laser beam along an optical axis into or onto the eye; a contact glass which is arranged following the focusing optics and can be placed on the eye, and a safety mechanism holding the contact glass movable in such a manner that it retracts when a force is directed onto the contact glass counter to the direction of incidence of the laser beam, wherein the beam-deflecting unit is arranged in the entrance pupil of the focusing optics, with respect to a deflecting element being effective for said one axis of deflection, and the safety mechanism couples the contact glass, the focusing optics and the deflecting element such that, during retraction, the deflecting element remains in the entrance pupil and the length of the light path between the deflecting element and the contact glass is constant.

According to the invention, the object is also achieved by a laser treatment apparatus for ophthalmic surgery, said apparatus comprising a contact glass which can be placed on the eye and through which a treatment laser beam is incident, and a safety mechanism holding the contact glass movable in such a manner that it retracts, when a force is directed onto the contact glass counter to the direction of incidence of the laser beam, wherein the safety mechanism comprises a detecting unit, which monitors retraction of the contact glass and which interrupts laser treatment operations of the laser treatment apparatus in case of a contact glass movement exceeding a threshold value.

Thus, the invention fundamentally deviates from the concept pursued by the prior art, which consists in compensating for any eye movements by a resilient support of the contact glass, and provides a contact glass which is rigid under certain basic conditions. In a first version of the invention, this rigidity is embodied such that the contact glass is movable only above a limit value of force. Thus, optimal optical conditions are ensured during irradiation of the eye with the treatment laser beam, and at the same time, compression of the eye is prevented, because the limit value of force causes a sort of panic release mechanism.

In another version of the invention, the rigidity of the contact glass does not relate to the eye, but to the mutual position of the contact glass, the focusing optics and the deflecting element. The coupling of the safety mechanism having this effect now allows movement of the contact glass due to eye or head movements of the patient, but now these movements have no effect on the optical properties of the focusing of the treatment laser beam.

In a third version of the invention, the rigidity of the contact glass provided for according to the concept of the invention is achieved in a functional manner. Laser treatment operation is interrupted if the contact glass is moved beyond a certain maximum amount.

Thus, the above-mentioned solutions provided by the invention realize different variants of the same inventive concept, namely to cause rigidity of the contact glass by means of a safety mechanism, said rigidity preventing unwanted defocusing or faulty positioning of the treatment laser radiation by eye movements or head movements. As mentioned above, said rigidity can be realized either structurally, with respect to the eye or the optics of the laser treatment apparatus, or functionally. These three approaches will be referred to hereinafter as the first variant (retraction of the contact glass above a limit value of force), the second variant (coupling of the contact glass, the focusing optics and the deflecting element) and the third variant (abortion of laser treatment if a movement of the contact glass exceeds a threshold value), respectively.

All three variants have in common that they prevent bruising of the eye. If there is danger of bruising, the contact glass and the patient are moved apart. This fact is referred to herein as retraction. This means, on the one hand, that the contact glass as well as possibly further parts of the laser treatment apparatus are moved away from the desired position of the patient. On the other hand, this term, of course, also covers a kinematically reversed approach, wherein the patient is moved away from the contact glass. From the patient's view, this is also a retraction of the contact glass, which justifies the generalization made herein.

Of course, the variants of the invention can also be combined with each other. This also applies to any embodiments and improvements.

In the first variant of the invention, an increase in the pressure which the patient exerts on the laser treatment apparatus, for example by his eye, only leads to a retraction of the contact glass if the limit value of force has been exceeded. Bruising of the eye is excluded if a suitable limit value of force is selected, and at the same time optimal operation is achieved under normal conditions.

In a particularly simple construction, the limit value of force is caused by an elastic force or weight force. One possibility of achieving this, is for example, an elastic support for the patient on a bed, which support is selected such that the patient's bed retracts upon an apparent increase in the patient's weight. An increased pressure of the eye on the contact glass manifests itself in such apparent increase in the patient's weight so that the desired retraction then occurs. The laser treatment apparatus or the optical component of this apparatus can remain spatially fixed. Instead of the described possibility of mechanical compensation, a corresponding closed-loop control can also be effected, of course, e.g. in the form of electronic closed-loop control.

In a kinematically reversed construction, which is comparatively more simple in mechanical terms, it is advantageous to mount the contact glass to a holding element, which is pressed against a stop of the housing by a force defining the limit value of force. In case of a contact pressure force exceeding the limit value of force, the contact glass can then be displaced relative to the housing so that the desired safety features are achieved. Retraction is then effected by the contact glass; the bed need not be moved for this purpose.

This can also be combined by mounting a force sensor to the holding element but effecting retraction through movement of the bed.

In an advantageous further embodiment of the invention, laser treatment can be continued even if the contact glass retracts, as long as certain basic conditions are complied with. For this purpose, retraction not only of the contact glass, but also of the relevant components of the optics by which the treatment laser beam is focused into or onto the eye is convenient. Therefore, the holding element which is mounted to the contact glass preferably also carries focusing optics which focus the treatment laser beam into or onto the eye. When retracting, the contact glass and the focusing optics then move together.

The limit value of force is conveniently set such that bruising of the eye is definitely prevented. A suitable value for this purpose is approximately 1 N.

The first variant of the invention is suitable not only to prevent damage caused by a patient's fault, but apparatus malfunction can also be checked thereby. During laser treatment, the patient is usually supported on a bed. A height adjustment unit allows adjustment of the distance between the laser treatment apparatus or the contact glass, respectively, and the patient. The safety mechanism according to the invention reliably prevents malfunction of this height adjustment mechanism resulting in bruising of the eye. If, for example, the height adjustment mechanism moves the patient too far towards the contact glass, the safety mechanism automatically causes retraction of the contact glass before there is a risk of the eye being squashed.

The second variant of the invention ensures that retraction of the contact glass has as little effect as possible on the optical quality with which the treatment laser radiation is introduced into the eye. Since in a laser treatment apparatus the laser treatment beam is guided to a great diversity of points (e.g. during the above-mentioned correction of visual deficiencies), three-dimensional shifting of the focus of the laser beam is usually required. This regularly requires deflecting elements in the form of two scanners, for example galvanometer scanners, for lateral movement of the laser focus.

In a simple construction, optical errors which occur during retraction of the contact glass can be minimized by rigidly connecting the contact glass and the focusing optics which focus the treatment laser beams into the eye such that they retract together. If a beam path section which is insensitive to changes in the length of the optical path, for example a parallel or near parallel beam path, is additionally arranged preceding the focusing optics, the optical errors occurring during retraction of the unit consisting of the focusing optics and the contact glass are automatically small.

In order to minimize errors induced by retraction of the contact glass, it is generally advantageous if the length of the light path following the deflecting element remains unchanged even during retraction. Otherwise, the distance in a projecting lens would change, which would be equal to a change in the effective focal length of the entire system. In particular, curved contact glasses, which have a concave curvature on the side facing towards the patient and which thus only add little to the internal pressure of the eye, would be difficult to use. Instead, contact glasses would have to be used, which flatten the front surface of the eye and are, therefore, disadvantageous with a view to keeping the internal pressure of the eye as constant as possible. Therefore, further minimizing is achieved if the contact glass, the focusing optics and at least one of the deflecting elements of the beam-deflecting unit are connected to form one single unit, and the safety mechanism causes longitudinal guiding of this unit.

The second variant of the invention then keeps the distance between the deflecting unit and the focus of the treatment laser radiation constant. If the axial position of the laser focus were shifted, unpredictable side effects could appear in the patient's cornea. In the worst case, a laser effect could even damage the epithelium or the endothelium.

The deflecting elements, e.g. AOD or scanners, are favorably arranged in pupil planes of the optics. In most cases, they effect beam deflection about two mutually perpendicular axes. However, other approaches, e.g. using a tumbling mirror, are also possible, if they effect 2-dimensional beam deflection. Common scanners operate by reflection at surfaces which are variable with respect to their clearance angle relative to the beam path. This has the effect that the entire beam path is folded at an angle at the scanners. In doing so, folding angles of approximately 90° are preferably realized. It is advantageous to design one of said bends such that part of the optical system is supported there rotatable about an axis. Retraction of the contact glass can then be achieved by rotating the optical system about said bend, so that the subsequent beam path is only pivoted, in principal, but otherwise does not change. If another deflection of the beam path, e.g. by 90°, is provided at this bend, retraction of the contact glass is realized as a pivoting movement about the axis of rotation located in the first bend. This enables pivoting of the subsequently arranged optics about the bend and, thus, a retraction of the contact glass without any changes appearing in the beam path.

Therefore, it is preferred that the light path of the laser beam be deflected at least once following the entrance pupil of the focusing optics and that the safety mechanism cause a joint rotary or pivoting movement of the contact glass, the focusing optics and the deflecting element during retraction. A particularly convenient construction is one in which the contact glass, the focusing optics and the deflecting element are rigidly connected to form an arm and the safety mechanism comprises a rotary support for the arm with the axis of rotation in the plane of the deflecting element. The arrangement of the axis of rotation at the deflecting element has the advantage that, during rotation or pivoting, no disadjustments are generated with respect to deflection.

However, a weight compensation may be necessary, because the rotary or pivoting movement requires the entire optical unit to be raised from the contact glass up to the pupil with the deflecting element. Therefore, it is favorable for this embodiment to provide corresponding balancing weights, reducing the force required to raise the arm and thus to retract the contact glass.

This embodiment is a variant of a generally preferable safety mechanism comprising a weight force compensation unit, in particular in the form of a counterweight or a spring element. If it is desired to combine the advantages of the first or second variants, the weight force compensation unit can conveniently set the limit value of force. In particular, it is possible for the arm to be supported by the housing of the laser treatment apparatus at the limit value of force.

Another approach involves placing the axis of rotation in the beam path at the location of the weight center of gravity, because, in doing so, a balanced structure and, consequently, a low force for the retraction of the contact glass is automatically achieved.

In the third variant of the invention, a detecting unit is provided for functional rigidity of the contact glass, which unit blocks the laser treatment operation upon a contact glass movement exceeding a threshold value. In this case, the threshold value can be selected according to different criteria. Depending on the design of the laser treatment apparatus, the threshold value can be selected in the sense of an emergency deactivation, which deactivates just before an inadmissibly great load on the eye, or may serve as a quality-ensuring feature and may consider the optical errors caused by said movement.

If the threshold value is selected such that it should prevent an inadmissibly high eye pressure, deactivation is effected before retraction of the contact glass reaches a mechanically determined end of said movement. Even after the threshold value has been exceeded, counter measures can still be initiated without the contact glass abutting at the end of its movement. For example, a height adjustment mechanism of the patient's bed can be deactivated or the patient's bed can be quickly lowered.

Thus, one of the counter measures consists in actively moving the contact glass and the eye apart. Therefore, it is preferred that the safety mechanism comprise a drive for active retraction of the contact glass and that a control unit control the drive to actively retract the contact glass in case of a force exceeding the limit value of force or a contact glass movement exceeding the threshold value, respectively.

In the case of the above-mentioned rotatable or pivotable optical arrangement of the second variant, the drive will usually initiate a pivoting or rotary movement, in particular rotating the arm mentioned above with respect to the second variant.

The detecting unit may use a light barrier located near a mechanical stop for the path of movement of the contact glass. Of course, a multi-level stepwise response detecting unit or continuous monitoring of the position of the contact glass is also possible according to the invention.

One possibility of additionally detecting that a desired maximum movement is exceeded consists in sensing at the mounting mechanism by which the eye is fixed to the contact glass. For this purpose, a vacuum is conventionally used. The detecting unit may then sense the pressure in the vacuum system and thus determine an inadmissible movement of the eye relative to the contact glass.

Due to the human physiognomy an eye movement directed towards the contact glass automatically involves a movement of the head. Therefore, it is possible to sense the force directed towards the contact glass not only at the eye, but also at the patient's body, preferably at the head. This procedure gives further protection to the eye. Therefore, it is convenient for all the above mentioned variants if a supporting unit is provided comprising a support that can be applied to the patient's body and is coupled to the safety mechanism such that a certain force on the support opposed to the direction of incidence of the laser beam also causes retraction of the contact glass. In the third variant, the detecting unit may detect pressure on the support.

The above summary is not intended to describe each illustrated embodiment or every implementation of the subject matter hereof. The figures and the detailed description that follow more particularly exemplify various embodiments.

BRIEF DESCRIPTION OF THE DRAWINGS

Subject matter hereof may be more completely understood in consideration of the following detailed description of various embodiments in connection with the accompanying figures, in which:

FIG. 1 shows a schematic perspective view of a laser treatment apparatus for treatment of a patient lying on a patient's bed;

FIG. 2 shows a schematic partial view of the beam path of the laser treatment apparatus of FIG. 1, viewed against the patient's viewing direction;

FIG. 3 shows a representation of the beam path of FIG. 2 in a plane rotated by 90°, i.e. as seen by a surgeon sitting behind the patient;

FIGS. 4 and 5 show representations of a laser treatment apparatus similar to that of FIG. 3 in a similar view as in FIG. 3;

FIGS. 6 and 7 show representations of a further modified laser treatment apparatus in a view similar to those of FIGS. 4 and 5;

Figure 8:
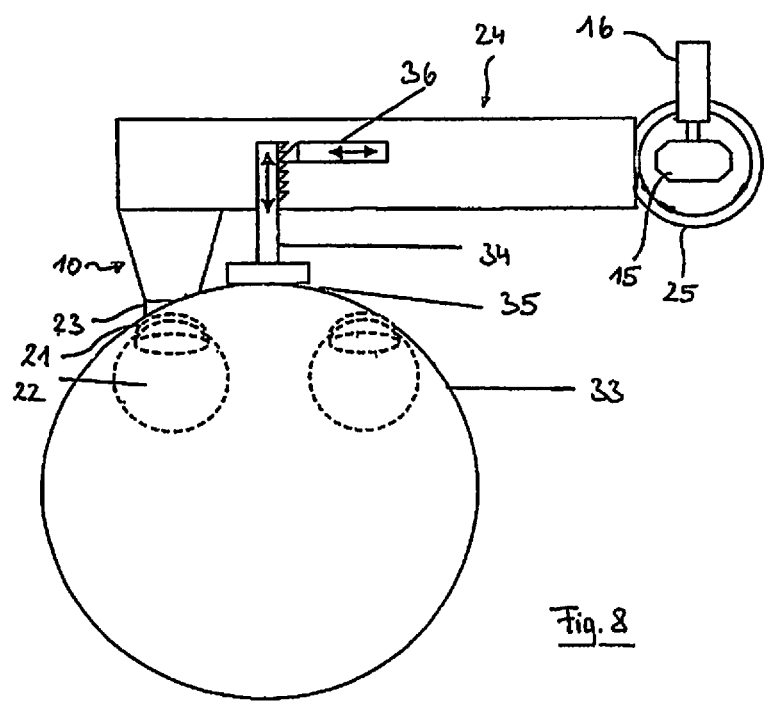
FIG. 8 shows a schematic representation of the laser treatment apparatus of FIG. 1 with a modified construction in a view similar to that of FIG. 3.

While various embodiments are amenable to various modifications and alternative forms, specifics thereof have been shown by way of example in the drawings and will be described in detail. It should be understood, however, that the intention is not to limit the claimed inventions to the particular embodiments described. On the contrary, the intention is to cover all modifications, equivalents, and alternatives falling within the spirit and scope of the subject matter as defined by the claims.

DETAILED DESCRIPTION OF THE DRAWINGS

Various embodiments of systems, devices, and methods have been described herein. These embodiments are given only by way of example and are not intended to limit the scope of the claimed inventions. It should be appreciated, moreover, that the various features of the embodiments that have been described may be combined in various ways to produce numerous additional embodiments. Moreover, while various materials, dimensions, shapes, configurations and locations, etc. have been described for use with disclosed embodiments, others besides those disclosed may be utilized without exceeding the scope of the claimed inventions.

Persons of ordinary skill in the relevant arts will recognize that the subject matter hereof may comprise fewer features than illustrated in any individual embodiment described above. The embodiments described herein are not meant to be an exhaustive presentation of the ways in which the various features of the subject matter hereof may be combined. Accordingly, the embodiments are not mutually exclusive combinations of features; rather, the various embodiments can comprise a combination of different individual features selected from different individual embodiments, as understood by persons of ordinary skill in the art. Moreover, elements described with respect to one embodiment can be implemented in other embodiments even when not described in such embodiments unless otherwise noted.

Although a dependent claim may refer in the claims to a specific combination with one or more other claims, other embodiments can also include a combination of the dependent claim with the subject matter of each other dependent claim or a combination of one or more features with other dependent or independent claims. Such combinations are proposed herein unless it is stated that a specific combination is not intended.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

For purposes of interpreting the claims, it is expressly intended that the provisions of 35 U.S.C. § 112(f) are not to be invoked unless the specific terms "means for" or "step for" are recited in a claim.

FIG. 1 shows a laser treatment apparatus in the form of a laser-surgical treatment station 1. It comprises a bed 2 on which a patient (not shown) is made to lie down during treatment. A laser unit 3 comprising a treatment head 4 is arranged beside and above the bed. The distance between the bed 2 or the patient lying thereon, respectively, and the treatment head 4 can be adjusted by a height adjustment unit 5 provided at the bed 2. The treatment head 4 is arranged on a cantilever 6 of the laser unit 3 such that it protrudes beyond a patient's head.

A surgeon can survey the progress of treatment through a microscope eyepiece 7 provided at the cantilever 6. A keyboard 8, as well as a monitor 9, serve to adjust parameters of the laser treatment method. The laser-surgical treatment station 1 is controlled by a computer C and is intended for ophthalmic correction of visual deficiencies.

The treatment head 4 has a nozzle 10, at which a treatment laser beam exits, and which nozzle contacts the eye for treatment. As will be explained below, the treatment head 4 comprising the nozzle 10 is movably supported within the cantilever 6 so that further space for movement exists between the nozzle 10 and a patient lying on the bed 2, or his eye respectively, in addition to the adjustability moved by the height adjustment unit 5.

FIG. 2 shows a detail of the treatment beam path 11, which is used by the laser-surgical treatment station 1 in order to focus treatment laser radiation L in the eye of the patient, to thereby generate optical breakthroughs and to ultimately effect correction of visual deficiency. The laser unit 3 comprises a laser emitting the treatment laser radiation L and expansion optics expanding the treatment laser radiation L.

These two elements are of no further relevance to the safety function of the laser-surgical treatment statement 1, which function is to be explained herein, and are therefore not shown in the Figures. The expansion optics include axially displaceable elements so that the laser focus can be shifted in an axial direction with the cornea.

Following the expansion optics, a first scanner is arranged comprising a scanning mirror 12, which is driven by a motor 13 to be pivotable about a first deflecting axis S1. The first scanning mirror 12 is located in a pupil of an optical system which will be explained later. Following the first scanning mirror 12, the pupil is imaged at elements 14 to ensure that the first scanning mirror 12 is located in a pupil of the optical system. In a further pupil lies a second scanning mirror 15, which is also driven by a motor 16. The axis of rotation of the second scanning mirror 15 is perpendicular to the deflecting axis S1 of the first scanning mirror 12. The second mirror 15 rotates about a second deflecting axis S2, shown in broken lines in FIG. 3. The deflecting axes S1 and S2 of the two scanning mirrors 12 and 15 are at right angles to each other.

Arranged following the second scanning mirror 15 are scanning optics 17, in whose pupil the second scanning mirror 15 is located and whose beam path is deflected into the nozzle 10 by a beam splitter 18. The nozzle 10 contains focusing optics 20 which focus the laser radiation L via a contact glass 23 into the cornea 21 of the patient's eye 22. The beam splitter 18 couples in an observation beam path 19 for the microscope eyepiece 7. At the same time, it deflects the beam path after the second scanning mirror 15 by 90°.

The scanning optics 17, the beam splitter 18, the focusing optics 20 and the contact glass 23 form an arm 24. The arm 24 is mounted to a rotary joint 25 together with the motor 16 and the scanning mirror 15. As a result, the arm 24 is pivotable about the rotary joint. The pivoting axis is located in the pupil, in which also the scanning mirror 15 is arranged, and extends perpendicular to the deflecting axis S2. Pivoting of the arm 24 consequently moves the contact glass 23 away from the cornea 21.

The scanning optics of the embodiment according to FIGS. 2 and 3 is mounted to a support 26 and is thus combined to the arm 24. This arm is connected to the rotary joint 25 in the form of a ball bearing. The axis of the ball bearing—for the sake of stability, a plurality of bearings can also be used on a common axis—is identical with the optical axis of the preceding pupil imagery 14. For example, a very large ball bearing having a large diameter can be used and placed directly on the mount of the pupil imagery 14. Thus, simple centering of the rotary joint 25 relative to the optical axis of the pupil imagery 14 is achieved, and the pivoting axis is located exactly in the pupil plane. The mounting of the second scanner 15 to the rotary joint provided here, which mounting, of course, is understood to be optional, ensures that the deflecting axes S1, S2 of the two scanners 12, 15 remain perpendicular to each other even when the arm 24 is raised and the beam reflected by the second scanning mirror 15 nevertheless always passes through the scanning optics 17 in a predetermined direction even when the arm 24 is pivoted.

Of course, it is alternatively possible to also have the pupil imaging elements 14 rotate together with the scanning optics 17, i.e. with the arm 24. This allows to realize a great length of guidance for the axis of rotation, thus achieving greater accuracy in guiding. In a further embodiment of this approach the entire optical unit, including laser(s), rotates. Such embodiment is favorable in terms of stability of the entire optical arrangement, but the forces of inertia which have to be overcome in order to initiate retraction of the contact glass increase with the mass of the supported unit.

In a further embodiment fiber coupling between the laser and its expansion optics is used. In this case all remaining elements of the optics are mounted on the pivotable supporting unit. Advantageously a chirp caused by the fiber is compensated for by a compressor unit either before entering the fiber or thereafter. The compressor unit is preferably arranged preceding the fiber, because the peak performance in the fiber is reduced thereby and light intensity-dependent damage to the fiber is avoided. At the same time self-phase modulation is reduced.

The construction of FIGS. 2 and 3 in the laser-surgical treatment station 1 of FIG. 1 allows the patient to push away the contact glass 23, which is being mounted to his eye by means of a vacuum, for example. The contact glass 23 can move away from the eye together with the focusing optics 20 and the scanning optics 17 and relieve the eye in order to avoid bruises. However, due to the mass of the elements to be moved initiation of said movement may require a force which cannot be applied via the patient's eye alone without auxiliary means.

Therefore, in the case of bulky optical structures, an embodiment as shown in FIGS. 4 and 5 is provided. In this case the arm 24 is stiffened by the support 26 to which the scanning optics 17, including the beam splitter 18 and the nozzle 10, are mounted. Further, a spring suspension 27 reducing the static forces is effective at the free end of the support 26. The arm 24 or the support 26, respectively, is further supported by the cantilever 6 such that it contacts the latter with a defined force. This bearing load is set by the suspension 27.

Thus, by exerting pressure on the contact glass 23, the patient can push the arm 24 on the support 26 away from himself using comparatively little force, so that the arm reaches the raised position shown in FIG. 5. It is merely required to overcome the bearing load. The force required to do so is set such that bruising of the eye is avoided. For instance, said force is 1 N.

FIG. 5 further clearly shows that the scanning mirror 15 rotates along with the pivoting of the arm 24. Thus, the coupling of the laser radiation from the scanning mirror 15 into the scanning optics 17 remains unchanged even if the support 26 is deflected and the contact glass 23 is thus raised.

However, the construction of FIGS. 4 and 5 cannot compensate for dynamic forces which are required in order to initiate rotation of the arm. Such dynamic forces appear as forces of inertia, when the patient moves towards the contact glass, because the bed 2 is being moved upwards. For acceleration of the arm 24 which is required for the contact glass 23 to retract, an additional force is required which can lead to at least temporary squeezing of the eye. In order to avoid this effect, which becomes relatively large from a certain moment of inertia of the arm 24 mounted to the rotary joint 25, it is favorable to provide a mechanism which actively retracts the contact glass 23, i.e. which assists the eye during acceleration of the contact glass 23 on the arm 24. For this purpose, it is necessary for the construction described herein to actively raise the arm 24.

FIGS. 5 and 6 show an exemplary embodiment of such mechanism operating here by means of a vacuum. A vacuum cell is mounted to the rotatable end of the arm 24 at the support 26. If there is negative pressure in the vacuum cell, it contracts and raises the support 26 at its free end. This condition is shown in FIG. 7. By means of a sensor 29, which is provided here as a mechanical feeler 30 actuating a switch 31, a control unit 32 is switched on as soon as the patient raises the arm 24 by a certain minimum amount from the arm's lower position. The control unit 23 then activates the negative pressure drive 28 which raises the support 26 with the arm 24 and, thus, pulls the contact glass 23 away from the eye. A small movement of the scanning optics, thus, leads to actuation of the negative pressure drive.

In a modified form only a part of the scanning optics or an additional part mounted to different optics may be mounted axially moveable with the rest of the scanning optics. If this component is moved upwards by the pressure of the eye, a corresponding signal for the control unit 32 is derived, which in turn activates the negative pressure drive 28. In doing so, the valve actuation required for this purpose can also be effected directly by mechanical means or even electrically. Of course, sensing of the scanning optics' movement can also be effected contact-free, e.g. by light barriers or a capacitive distance sensors.

As an alternative to the negative pressure drive described here, any suitable drive is conceivable, of course, for example also one comprising electrically driven servo motors.

Instead of or in addition to actively driving the arm 24, support by way of a mechanical spacer can be used as shown in FIG. 8. The spacer comprises a stem 34, which can be placed in contact with the patient's head 33 and contacts the patents' forehead 35 when the contact glass 23 is in place. In doing so, the stem 34 is set such by a locking mechanism that it contacts the forehead 35 directly. The stem extends parallel to the direction of irradiation along which the laser treatment radiation L is incident in the contact glass 23 and the cornea 21 through the nozzle 10. As soon as the cornea 21 contacts the contact glass 23, the stem is displaced downwards, e.g. moved by the force of its own weight, such that it contacts the patient's forehead. In this position, it locks automatically or is externally locked. If the patient's eye 22 moves upwards now, the arm 24 is automatically raised by the stem 34.

In addition or as an alternative to the stem 34, support may also be effected directly at the patient's bed 2. Thus, inadvertent actuation of the height adjustment unit 5 is immediately converted to retraction of the contact glass 23 by pivoting of the arm 24.

It is also possible to cause actuation of the negative pressure drive 28 by purely pneumatic means. The feeler 30 then actuates a switch 31, which is provided as a valve and is located in a vacuum duct between a vacuum source, which corresponds to the control unit 32 in the drawing, and the negative pressure drive 28. The valve is opened when the feeler 30 has moved upwards, as is the case during a slight movement of the support 26 with the arm 24. When the valve is open, the negative pressure drive 28 is evacuated, contracts and thereby tilts the support 26 with the arm 24 upwards.

If the optics accommodated in the arm 24 have a suitable design, the suspension 27 is sufficient to avoid bruising of the patient's eye. Assuming a length of the arm of half a meter and realizing a moment of inertia of the arm 24 of 2 kg•m$^2$, an eye movement at 6 mm per second towards the contact glass 23, at a radius of curvature of 7.8 mm and a radius of curvature of the contact glass of 2 cm leads to a force of 0.3 N, if the eye is pushed in by 0.77 mm during acceleration of the contact glass 23. The contact glass 23 with the entire arm 24 is then accelerated to the speed of movement of the eye within a third of a second. Thus, it is evident that an external drive is not stringently required if the arm 24 is skillfully designed.

Figure 9:
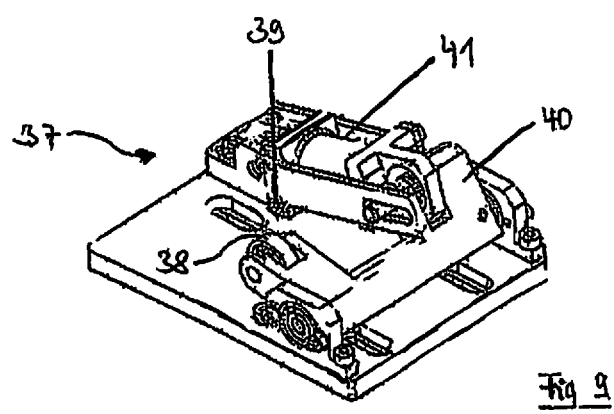
FIG. 9 shows a weight balancing mechanism provided in the laser treatment apparatus of FIG. 1.

FIG. 9 shows a possible design of a spring mechanism serving the function of the suspension 27. It is a supporting mechanism 37 which supports the arm 24 from below. The arm 24 is supported on a roll 38 which is connected to a spring 41 via a lever 40, said spring pushing the roll 38 upwards. The weight force of the arm 24 acting in the direction of the arrow 39 can be compensated for as desired, except for a residual bearing load, by suitably selecting or positioning the spring 41.

It is of absolutely no importance in the constructions described above whether the actuating movement is caused by the patient or by a movement of the bed 2. The arm 24 is always raised.

Figure 10:
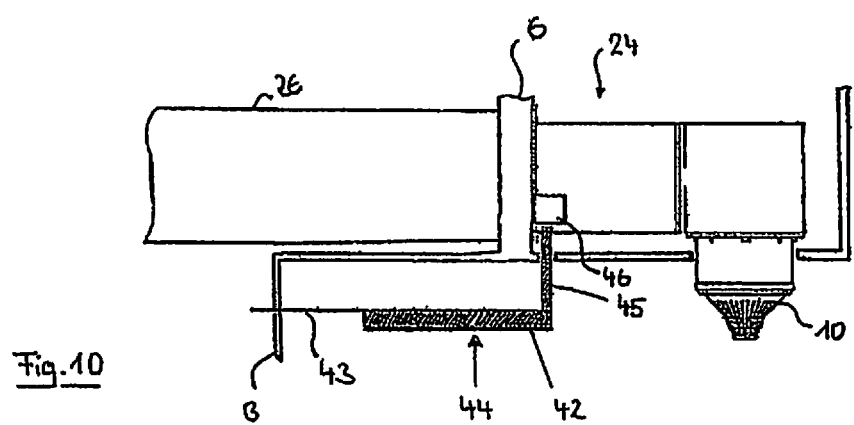
FIG. 10 shows a schematic representation of a laser treatment apparatus similar to that of FIG. 1, but in lateral reversal, comprising an additional safety mechanism in order to protect a patient against bruises.

FIG. 10 shows a further detailed view of an extension 6 of a laser-surgical treatment station similar to the construction shown in FIG. 1, although the representation in FIG. 10 is mirror-inverted relative to that chosen in FIG. 1. It is evident again that the arm 24 with the nozzle 10 is provided in the extension 6, of which merely some components of a housing B are shown. The arm 24 is pivotable with the support 26 relative to the extension 6 about a pivot point located to the left in FIG. 10, but not shown. In this pivotal movement, the nozzle 10 is raised relative to the housing B such that it retreats into the housing B. The arm 24 or the support 26, respectively, contacts the extension 6 at a support not illustrated. LRaising the extension 6 can be effected by a force acting on the nozzle 10 (via the contact glass 23).

In the construction of FIG. 10, a safety mechanism is additionally provided which also protects the patient's body from bruises caused by the arm 24. For this purpose, a baffle plate 42 is mounted to the housing B by means of a joint 43, which may be designed, for example, as a bendable attachment in the form of a steel plate. The baffle plate 42 is supported on the arm 24 or its support 26 by a ridge 45. A force acting on the baffle plate 42 in the direction of the arrow 44 thereby exerts an upward pressure on the arm 24. A position sensor 46 detects raising of the arm 24. A possible embodiment of this position sensor 46, which senses the displacement of the arm 24 relative to the housing B or the extension 6, respectively, is shown by way of example in FIG. 11.

Figure 11:
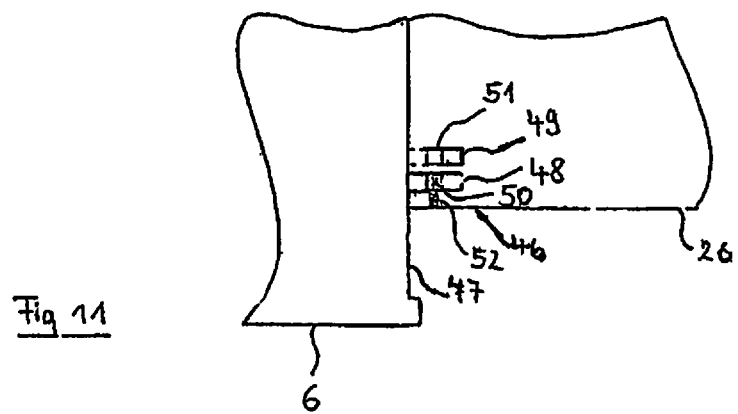
FIG. 11 shows an enlarged detail of FIG. 10.

As is evident from FIG. 11, light barriers 48 and 49 comprising slits 50 and 51 are mounted to a mounting surface 47 of the extension 6 on the housing side. Through these slits a position mark 42 can pass which is attached to the support 26 or to the arm 24, respectively. Thus, when the arm 24 is raised, the position mark 52 moves into the slot 50 and, if raised further, also into the slot 51. If the position mark 52 is located in the slot 50 or 51, respectively, of the light barrier 48 or 49, it generates a corresponding signal which is transmitted to a control unit (not shown), for example the computer C of the laser-surgical treatment station 1 (cf. FIG. 1). The computer C then controls a corresponding reaction of the system, for example deactivating the treatment laser radiation L or lowering of the patient's bed 2.

Figure 12:
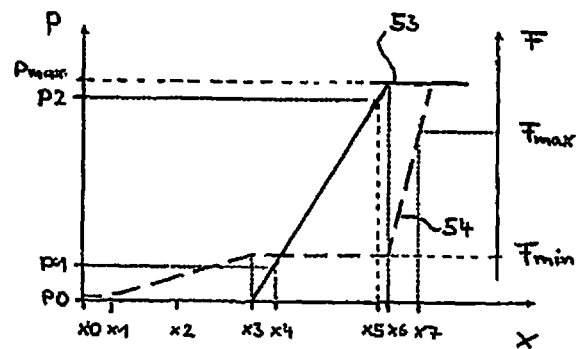
FIG. 12 shows a diagram illustrating the forces appearing at the eye during operation of a laser treatment apparatus according to FIG. 1.

FIG. 12 schematically shows an exemplary relationship between the position P of the arm 24 or of the nozzle 10, respectively, of the laser-surgical treatment station 1 and the force F on the eye of the patient, each as a function of the eye's position x, which is given for a patient lying on the bed 2 by the position of the height adjustment unit 5. When a patient is being prepared for treatment, a new, sterile contact glass 23 is first attached to the nozzle 10. Then, the patient is placed on the bed 2 whose height adjustment unit 5 is controlled by the surgeon at the laser-surgical treatment station 1. For this purpose, the computer C comprises a suitable input device, for example a joy stick, and controls the height adjustment unit 5 accordingly. At the beginning the height adjustment unit 5 is moved downwards, resulting in the location x0. At the same time, the nozzle 10 is located at its lowermost position P0, because the arm 24 contacts the extension 6 at the lower stop. The surgeon then moves the patient upwards by means of the height adjustment unit 5 until the patient's eye contacts the contact glass 23 at the location x1. The surgeon now slowly moves the patient further up, until the eye fully contacts the contact glass 23. This is the case at the location x2, which is characterized in that the vacuum for fixing the contact glass 23 to the cornea 21 can be applied.

In order for the cornea 21 to contact the internal surface of the contact glass 23 as completely as possible, the eye 23 presses against the contact glass 23 with a certain force. However, since this force is still weaker than the force $F_{min}$, by which the arm 24 is raised, the arm 24 continues to rest in this case.

Upon activating the vacuum, the computer C automatically raises the height adjustment unit 5 slightly, so that the bed 2 is still raised slightly above the location x2, in order to ensure secure fixation of the contact glass 23 to the cornea 21 by means of a vacuum. The height adjustment unit 5 or the patient's head, respectively, is thus located between the locations x2 and x3. The eye presses against the contact glass 23 with a force below the minimum force $F_{min}$, so that the arm 24 still remains in the position $P_0$, i.e. is not raised. The eye is fixed to the contact glass, and treatment can be started.

If the patient's head moves upwards during treatment, for example because the patient is moving his head, or due to an involuntary actuation of the height adjustment unit 5, the force on the arm 24 will not be equal to the minimum force $F_{min}$ with which the arm 24 contacts the cantilever 6, until the location x3 is reached. Upon a further upward movement of the head, the cantilever 24 will be raised. This case corresponds to the rising of graph 53 (shown as a solid line) in FIG. 12, and the arm 24 leaves its resting position P0. If the cantilever has reached the position P1, because the patients head, or in the case of a malfunction or faulty operation, the height adjustment unit 5 has reached the location x4, the first light barrier 48 will output a switching signal. Because the arm 24 can be lifted through the set force $F_{min}$, the force exerted on the eye, and, thus, the pressure on the eye does not increase any further.

The switching signal reached at position P1 causes the computer C to switch the laser beam L such that no treatment is effected anymore. For example, the laser can be switched off or the laser beam energy can be reduced such that no optical breakthroughs are generated anymore. Moreover, it is possible to output an alert to the surgeon, for example in the form of a corresponding display on the monitor 9.

Finally, a switching mechanism can be provided in the computer C, which mechanism automatically moves the height adjustment unit 5 downwards, i.e. to lower x-values, upon reaching position P1, in order to lead the eye back into the normal treatment region between x2 and x3. Once this has been achieved, the switching signal from the light barrier 48 changes back to the resting condition, normal treatment operation is resumed and the alert is deactivated. If the relative movement of the eye and the contact glass is caused only by moving the bed, the switching mechanism can be adapted to the x-values such that, for example, movement is effected upon reaching x3.

However, if the arm 24 moves further up due to a malfunction or a corresponding action by the patient and reaches position P2, the second light barrier 49 will respond and the computer C will then initiate an emergency shutdown, which deactivates the height adjustment unit 5 and moves it down, on the one hand, as well as deactivating the laser-surgical treatment station 1, except for the control, on the other hand. This happens in order to prevent that beyond the location x5 the location x6 is reached, where the arm 24 arrives at its maximum deflection at position $P_{max}$, at which no further retraction is possible. If the raising movement of the head still continued, the force on the cornea 21 or on the eye 22 would suddenly increase from the location x6 onwards, as clearly shown by the curve of force 24 of FIG. 12. At the location x7, the maximum admissible force $F_{max}$ on the eye 22 would be reached and there would be danger of bruising.

Due to the emergency shutdown of the laser-surgical treatment station 1 effected at the location x5 or the position P2, bruising of the eye 22 is avoided even if the patient panics.

Since the baffle plate 42 is located below the cantilever 6 in the embodiment according to FIG. 10, bruising of the patients body is also avoided, which may occur if the height adjustment unit pushes the patient against the cantilever 6.

Figure 13:
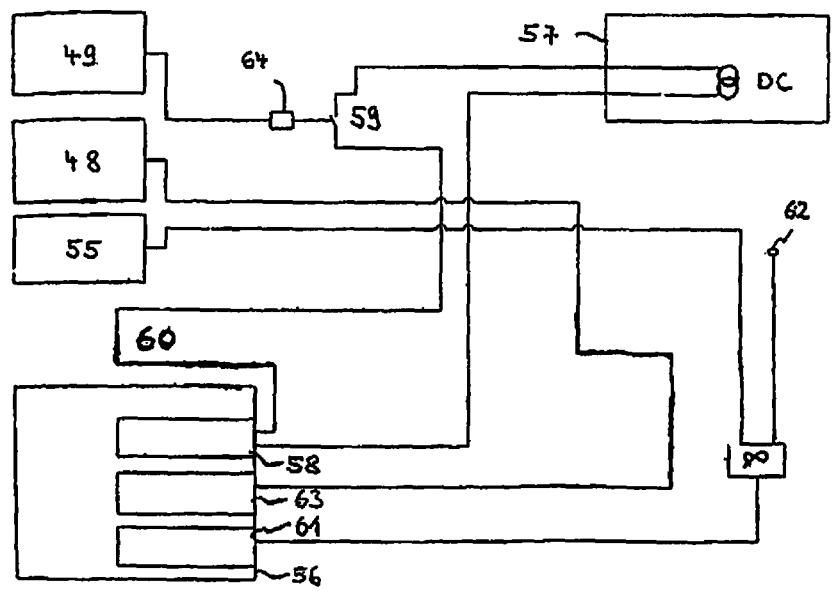
FIG. 13 shows a schematic representation of a circuit diagram for the laser treatment apparatus of FIG. 1.

FIG. 13 shows a circuit which may be realized for example by the computer C in order to carry out the method of protection described with reference to FIG. 12. FIG. 13 shows the exemplary light barriers 48 and 49 of FIG. 11 generally as sensors sensing whether the arm 24 has reached positions P1 or P2, respectively. FIG. 13 further schematically illustrates a suction pressure sensor 55, which monitors whether the vacuum used for suction of the contact glass 23 is in a range of values in which reliable suction of the eye 22 to the contact glass 22 is given. The sensors as well as the vacuum sensor 55 act on a drive 56 of the height adjustment unit 5 in a manner yet to be described. The drive 56 is supplied by a d. c. source 57, which feeds a power supply 58 of the drive 56. The current source 57 is connected to the power supply 58 by two lines. Two emergency switches 59 and 60 are switched into a feed line, which open upon actuation and which are closed in their deactivated condition.

The emergency switch 59 is controlled by the second light barrier 49 and the emergency switch 60 serves as a mechanical emergency switch for the surgeon, so that the connection between the current source 57 and the power supply 58 of the drive 56 can be interrupted at any time, and thus, the drive 56 can be deactivated.

The drive 56 further comprises a blocking mechanism 61 whose actuation deactivates the drive 56. Such blocking occurs if a vacuum sensor 62 indicates that the suction of the eye 22 to the contact glass 23 is switched on and also if the vacuum sensor 55 indicates suction of the eye. In this condition the blocking mechanism 61 prevents any further action of the height adjustment unit 5 by the drive 56 because a shift in the height adjustment unit 5 may not be required and may even cause damage when the eye is subject to suction.

The drive 56 is further provided with a blocking mechanism 63, which is controlled by the first light barrier 48 and, in parallel with the locking mechanism 61, prevents any activity of the drive 56 when the first light barrier 58 indicates that the arm 24 has reached position P1. This prevents the height adjustment unit 5 inadvertently being actuated and raising the patient, which would be possible if the vacuum were cut by a movement of the patient and the vacuum sensor 55 thus no longer signaled that the eye is subject to the correct suction. Thus, for example when the patient moves sideways or upwards, operation of the drive 56 and, consequently, action of the height adjustment unit 5 is also prevented.

The parallel provision of the locking mechanism 61 as well as the blocking mechanism 63 thus allows to effect closed-loop control by means of the height adjustment unit 5, said control guaranteeing secure suction of the eye.

The second light barrier 49, which emits a signal when the arm is in position P2, is connected to the emergency switch 59 via a relay 64. If the second light barrier 49 emits a signal indicating position P2, the emergency switch 59 will be opened and the drive 56 will be de-energized. Depending on the design of the drive 56, the bed 2 then remains at the presently set height or smoothly glides downwards.

The described system according to the invention avoids bruising of the eye in a laser-surgical treatment station, due to the component which contacts the eye automatically executing a deflecting movement, if the patient is lifted or raises his head. At the same time, the deflecting movement is advantageously realized such that the optical quality of the treatment during such deflection remains unchanged, if possible. Moreover, it is ensured by corresponding sensors and control mechanisms that a movement leading to bruising of the eye cannot occur.

The invention claimed is:

1. A laser treatment method for ophthalmic surgery at an eye of a patient, comprising:
    placing the patient on a bed comprising a headrest;
    positioning a nozzle over the patient's eye at which nozzle a treatment laser beam exits towards the eye;
    placing a contact element onto a part of the patient;
    monitoring a force that occurs between the contact element and the part of the patient when the contact element is on the part of the patient during a laser procedure;
    detecting, during a first portion of the laser procedure, that the force that occurs between the contact element and the part of the patient is below a limit value of force and fixing the headrest and the nozzle relative to each other; and
    detecting, during a second portion of the laser procedure, that the force that occurs between the contact element and the part of the patient exceeds the limit value of force and moving the headrest and the nozzle apart.

2. The laser treatment method as claimed in claim 1, further comprising retracting the nozzle into a portion of a laser treatment apparatus when the force exceeds the limit value of force.

3. The laser treatment method as claimed in claim 1, further comprising setting the limit value of force by at least one of the following: a pre-set elastic force and a pre-set weight force.

4. The laser treatment method as claimed in claim 1, further comprising mounting the contact element to a holding element and further comprising pressing the holding element against a stop of a housing with a force defining the limit value of force.

5. The laser treatment method as claimed in claim 4, further comprising focusing the treatment laser beam into or onto the eye by using focusing optics provided in the holding element.

6. The laser treatment method as claimed in claim 1, wherein the limit value of force is one Newton.

7. The laser treatment method as claimed in claim 1, further comprising providing the contact element as a patient interface at the nozzle and guiding the treatment laser beam through the patient interface.

8. The laser treatment method as claimed in claim 7, wherein the force that occurs between the contact element and the part of the patient is in a direction substantially counter to the direction of incidence of the laser beam.

9. The laser treatment method as claimed in claim 1, further comprising:
    variably deflecting the treatment laser beam by using a deflection element comprising at least one axis of beam deflection;
    focusing the laser beam along an optical axis into or onto the eye by using a focusing optics comprising an entrance pupil, and positioning the deflecting element substantially in the entrance pupil of the focusing optics;
    wherein the contact element is a patient interface which is provided at the nozzle and placed onto the eye, further comprising guiding the treatment laser beam through the patient interface, and
    further comprising coupling the contact element, the focusing optics and the deflecting element such that, when moving the headrest and the nozzle apart, the deflecting element remains substantially in the entrance pupil and the length of a light path between the deflecting element and the patient interface is kept substantially constant.

10. The laser treatment method as claimed in claim 9, further comprising retracting the patient interface when the force exceeds the limit value of force.

11. The laser treatment method as claimed in claim 10, wherein the patient interface, the focusing optics, and the deflecting element form a substantially rigidly connected unit, the method further comprising providing a longitudinal guide of that unit for retracting the patient interface.

12. The laser treatment method as claimed in claim 10, further comprising folding the light path at least once and moving the patient interface, the focusing optics and the deflecting element jointly and in a rotary or pivotal manner during the retraction.

13. The laser treatment method as claimed in claim 12, wherein the patient interface, the focusing optics, and the deflecting element form a substantially rigidly connected arm, the method further comprising providing a rotary support for the arm having an axis of rotation lying in a plane comprising the entrance pupil.

14. The laser treatment method as claimed in claim 13, wherein the rotary support for the arm is set at the limit value of force so that the arm rotates about the axis of rotation in response to the force that occurs between the contact element and the part of the patient exceeding the limit value of force.

15. The laser treatment method as claimed in claim 9, further comprising: providing a weight force compensating unit selected from a group consisting of a counterweight and a spring element.

16. The laser treatment method as claimed in claim 15, further comprising setting the limit value of force with the weight force compensating unit.

17. The laser treatment method as claimed in claim 1, further comprising providing the contact element to comprise a support and further comprising placing the support in contact with the patient's body.

18. The laser treatment method as claimed claim 1, further comprising moving the bed substantially along a direction of incidence of the treatment laser beam to move the headrest and the nozzle apart.

19. The laser treatment method as claimed in claim 1, further comprising moving the contact element with the nozzle in response to the force that occurs between the contact element and the part of the patient exceeding the limit value of force.

20. The laser treatment method as claimed in claim 19, further comprising driving the nozzle or the contact element and the patient apart actively when the force exceeds the limit value of force.

21. The laser treatment method as claimed in claim 20, further comprising driving the nozzle or the contact element and the patient apart actively by a pivotal or rotary movement.

22. The laser treatment method as claimed in claim 1, further comprising monitoring movement of the nozzle or of the contact element and interrupting laser treatment operation if movement exceeds a threshold value.

23. The laser treatment method as claimed in claim 22, further comprising driving the nozzle or the contact element and the patient apart actively when movement detected exceeds the threshold value.

24. The laser treatment method as claimed in claim 1, further comprising lowering the bed when force exceeds the limit value of force.

25. The laser treatment method according to claim 1, wherein the step of placing the contact element onto the part of the patient comprises mounting the contact element to a front face of an eye of the patient by establishing vacuum between the front face of the eye and the contact element.

26. The laser treatment method according to claim 25, wherein the step of moving the headrest and the nozzle apart when a force exceeding a limit value of force occurs is performed while the contact element is mounted to the front face of the eye.

* * * * *